United States Patent [19]

Langbein et al.

[11] 4,393,069
[45] Jul. 12, 1983

[54] 8-ARYLALKYL-3-PHENYL-3-NOR-TROPANOLS AND SALTS THEREOF

[75] Inventors: Adolf Langbein, Gau-Algesheim; Herbert Merz; Rainer Sobotta, both of Ingelheim am Rhein; Rudolf Bauer, Wiesbaden; Hans M. Jennewein, Walluf; Joachim Mierau, Mainz, all of Fed. Rep. of Germany

[73] Assignee: C. H. Boehringer Sohn, Ingelheim am Rhein, Fed. Rep. of Germany

[21] Appl. No.: 324,680

[22] Filed: Nov. 25, 1981

[30] Foreign Application Priority Data

Dec. 4, 1980 [DE] Fed. Rep. of Germany ....... 3045688

[51] Int. Cl.³ .................... C07D 401/02; A61K 31/46
[52] U.S. Cl. .................................... 424/265; 546/125; 546/127; 546/129; 546/130
[58] Field of Search ............... 546/125, 127, 129, 130; 424/265

[56] References Cited

U.S. PATENT DOCUMENTS

| 2,921,938 | 1/1960 | Wetteran .............................. 546/129 |
| 3,452,029 | 6/1969 | Childress et al. .................... 546/130 |
| 3,657,252 | 4/1972 | Kaiser et al. ......................... 546/127 |

FOREIGN PATENT DOCUMENTS

| 1174792 | 7/1964 | Fed. Rep. of Germany . |
| 837273 | 6/1961 | France ................................. 546/129 |
| 644115 | 10/1950 | United Kingdom ................. 546/127 |

Primary Examiner—Jane T. Fan
Attorney, Agent, or Firm—Hammond & Littell, Weissenberger & Muserlian

[57] ABSTRACT

Compounds of the formula

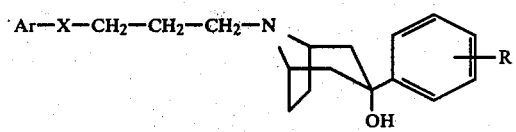

wherein Ar is

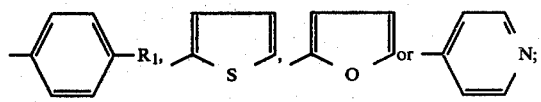

$R_1$ is hydrogen, fluorine, bromine, methyl or methoxy; X is $=CO$, $=CH-CN$, $=CH-OH$, $-O-$, $-S-$, $-NH-$,

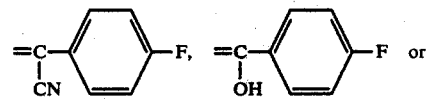

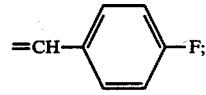

and
R is hydrogen, 4-fluoro, 4-chloro, 4-trifluoromethyl, 3-trifluoromethyl, 3-trifluoromethyl-4-chloro, 4-methyl or 4-methoxy;
and non-toxic, pharmacologically acceptable acid addition salts thereof. The compounds as well as their salts are useful as neuroleptics.

6 Claims, No Drawings

8-ARYLALKYL-3-PHENYL-3-NORTROPANOLS AND SALTS THEREOF

This invention relates to novel 8-arylalkyl-3-phenyl-3-nortropanols and non-toxic acid addition salts thereof, to methods of preparing these compounds, to pharmaceutical compositions containing them as active ingredients, and to a method of using them as neuroleptics.

More particularly, the present invention relates to a novel class of nortropanols represented by the formula

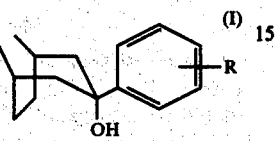

wherein
Ar is

$R_1$ is hydrogen, fluorine, bromine, methyl or methoxy;
X is =CO, =CH—CN, =CH—OH, —O—, —S—, —NH—,

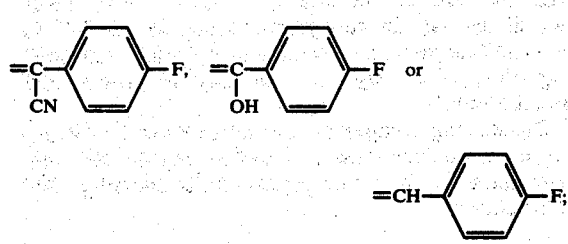

and
R is hydrogen, 4-fluoro, 4-chloro, 4-trifluoromethyl, 3-trifluoromethyl, 3-trifluoromethyl-4-chloro, 4-methyl or 4-methoxy;
and non-toxic, pharmacologically acceptable acid addition salts thereof.

A preferred subgenus thereunder is constituted by compounds of the formula I wherein
Ar is 4-fluoro-phenyl;
X is =CO, =CH—CN, =CH—OH or

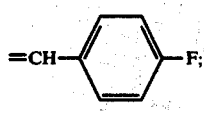

and
R is halogen;
and non-toxic, pharmacologically acceptable acid addition salts thereof.

A particularly preferred subgenus is constituted by compounds of the formula I wherein
A is 4-fluoro-phenyl;
X is =CO or =CH—CN; and R is halogen;
and non-toxic, pharmacologically acceptable acid addition salts thereof.

Compounds of the formula I wherein X is —CH—CN, =CH—OH,

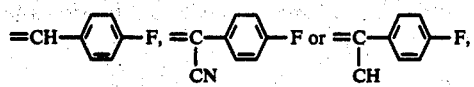

comprise an asymmetric carbon atom and therefore occur as racemates as well as in the form of their optical antipodes.

The compounds embraced by formula I may be prepared by the following methods:

METHOD A

By reacting a 3-phenyl-3-nortropanol of the formula

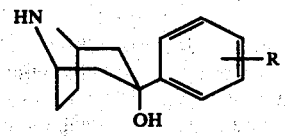

wherein R has the same meanings as in formula I, with an alkylating agent of the formula

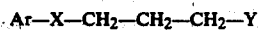

wherein
Ar and X have the same meanings as in formula I, and
Y is halogen or alkylbenzenesulfonyloxy, preferably chlorine, bromine or tosyloxy.

The alkylating agent is provided in the calculated amount or in excess of the stoichiometric amount, and the reaction is advantageously performed in the presence of an acid-binding agent such as triethylamine, dicyclohexylethylamine, sodium carbonate, potassium carbonate, calcium oxide or preferably sodium bicarbonate.

Although the use of a solvent is not necessary, it is more advantageous to perform the reaction in an inert solvent such as chloroform, toluene, ethanol, nitromethane, tetrahydrofuran or preferably dimethylformamide. The reaction temperature may vary within wide limits, but temperatures between 50° and 150° C., especially 100° C., are preferred. The addition of catalytic to molar amounts of potassium iodide or sodium iodide to the reaction mixture is of advantage.

METHOD B

For the preparation of a compound of the formula I wherein X is —O—, —S— or

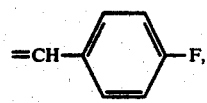

by reacting an 8-arylalkyl-nortropine-3-one of the formula

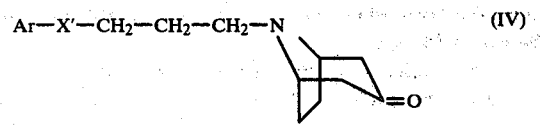 (IV)

wherein Ar has the same meanings as in formula I, and

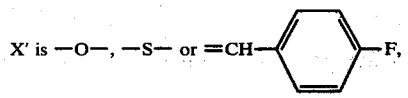

with a lithiumphenyl compound of the formula

 (V)

wherein R has the same meanings as in formula I.

The lithiumphenyl compound is provided in equimolar amount, and the reaction is performed in an inert solvent which does not contain active hydrogen atoms or groups which react with lithiumaryls, such as benzene, toluene, petroleum ether, or aliphatic or cycloaliphatic ethers; examples of such ethers are diethyl ether, tetrahydrofuran and dioxane.

The reaction is most advantageously performed at very low temperatures; the best yields are obtained if the reaction is carried out at temperatures between $-40°$ and $-15°$ C.

METHOD C

For the preparation of a compound of the formula I wherein X is

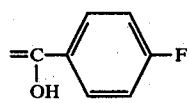

and R is 4-fluoro, by reacting an 8-aroylpropyl-nortropin-3-one of the formula

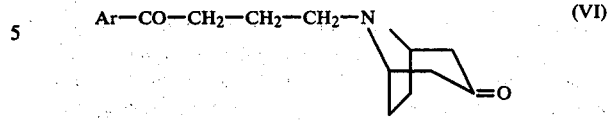 (VI)

wherein Ar has the same meanings as in formula I, with at least two mol-equivalents of 4-fluorophenyl lithium. The reaction conditions for this particular method arylation are the same as those described in method B.

METHOD D

For the preparation of a compound of the formula I wherein X is —CO—, by subjecting an 8-arylalkyl-3-phenyl-3-nortropanol of the formula

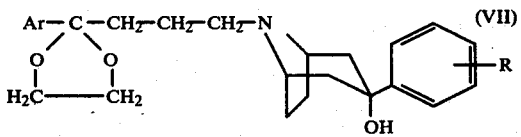 (VII)

wherein Ar and R have the same meanings as in formula I. to ketal cleavage with a dilute acid.

The ketal cleavage is preferably carried out in an aqueous organic solvent such as a lower alkanol. Dilute mineral acids such as hydrohalic acids or sulfuric acid.

The end products of the formula I obtained in accordance with methods A, B, C and D may be isolated from the reaction mixtures by means of known methods. If desired, the raw products may be purified by conventional methods, for instance by column chromatography, before they are crystallized as bases or acid addition salts.

The starting compounds of the formulas II, IV and VI needed for methods A, B and C, respectively, may be prepared by the routes shown in the following reaction scheme:

Route A

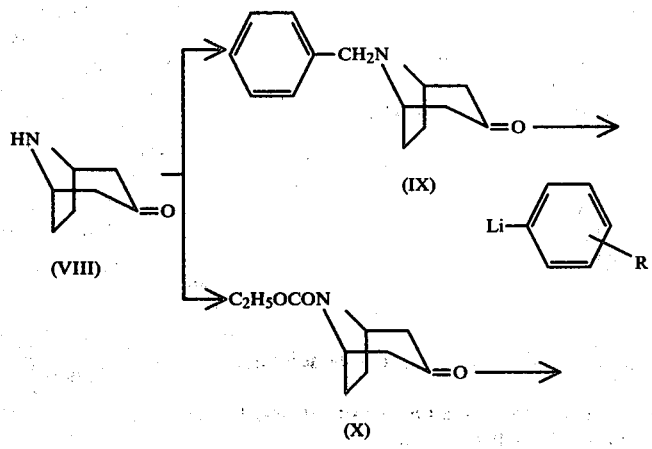

Route B

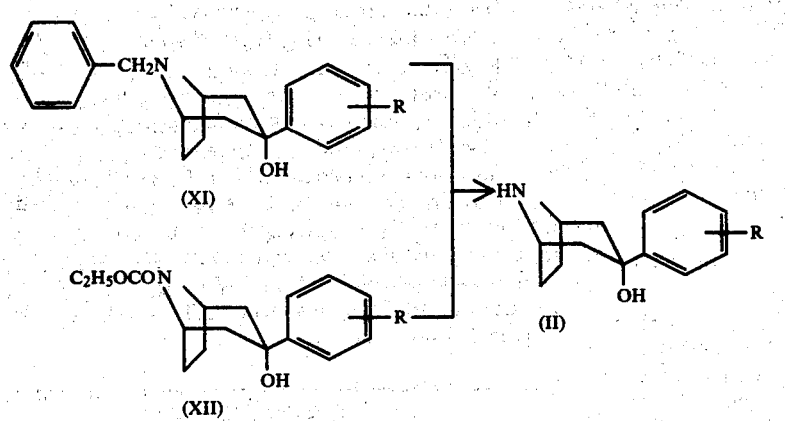

Nortropinone of the formula VIII is obtained by the process described in British Pat. No. 1,167,688. By benzylation (route A) or ethoxycarboxylation (route B) of nortropinone the substituted nortropinones of the formulas IX or X are obtained, from which the corresponding nortropanols of the formula XI or XII are prepared by reaction with a lithiumphenyl. The reaction is carried out in a solvent such as ether, petroleum ether, benzene or toluene. The reaction temperature must be kept within the critical range of $-35°$ to $-15°$ C.

In route A, the cleavage of the benzylated nortropanol of the formula XI into the nortropanol of the formula II is effected by catalytic debenzylation with a metal catalyst, such as palladium-on-charcoal, in the presence of a solvent such as an alcohol like methanol, ethanol or isopropanol, and under a pressure not exceeding 5 bar. The reaction temperature is variable but should not exceed 50° C.

In route B, the nortropanol of the formula II is obtained by hydrolysis of the ethoxycarboxylated nortropanol of the formula XII. The hydrolysis conditions are variable within wide limits, but potassium hydroxide or sodium hydroxide in a mixture of alcohol and water are preferably used. The reaction temperature range is also not critical, but refluxing is preferred.

The starting compounds of the formula VII are obtained by method A, i.e. by alkylation of a 3-phenyl-3-nortropanol of the formula II with an alkylating agent of the formula

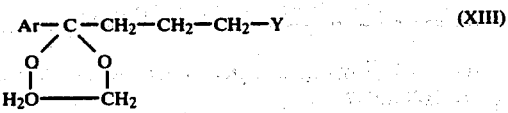

(XIII)

wherein Ar and Y have the meanings previously defined.

The compounds embraced by formula I are basic and therefore form addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxy-benzoic acid, p-amino-benzoic acid, phthalic acid, cinnamic acid, salicylic acid, ascorbic acid, methanesulfonic acid, 8-chloro-theophylline or the like.

The following examples illustrate the present invention and will enable others skilled in the art to understand it more completely. It should be understood, however, that the invention is not limited solely to the particular examples given below.

PREPARATION OF PRECURSORS AND STARTING COMPOUNDS

EXAMPLE A (a) 8-Benzyl-nortropinone

A mixture of 161.6 gm (1 mol) of nortropinone hydrochloride (prepared from tropinone by phosgene demethylation according to the method of British Pat. No. 1,167,688), 139.2 gm (1.1 mols) of benzyl chloride, 336.0 gm (4 mols) of sodium bicarbonate, 16.6 gm (0.1 mol) of potassium iodide and 1600 ml of absolute dimethylformamide was stirred for 1½ hours at 100° C. The solvent was then distilled off, the residue was suspended in 1.5 liters of ethyl acetate, and the suspension was vigorously shaken three times with 500 ml of water each. The ethyl acetate phase was dried over magnesium sulfate, filtered and concentrated by evaporation. The oily residue was dissolved in 700 ml of ethanol, and the solution was mixed with 390 ml of 2.5 N ethanolic hydrochloric acid. The crystallized salt was suction-filtered off after cooling, washed once with 50 ml of ice-cold ethanol and 3 times with 50 ml each of a 1:1 ethanol/ether mixture. 201.4 gm of white crystals were obtained with a yield of 80% of theory and a melting point of 195° to 196° C.

| | $C_{14}H_{17}NO \times HCl$ (mol. wt.: 251.75) | | | |
|---|---|---|---|---|
| | C | H | N | Cl |
| Calc.: | 66.79%; | 7.21%; | 5.56%; | 14.08% |
| Found: | 66.40%; | 7.58%; | 5.06%; | 14.11%. |

(b) 8-Ethoxycarbonyl-nortropinone

A mixture of 161.6 gm (1 mol) of nortropinone hydrochloride, 252.7 gm (2.5 mols) of triethylamine and 1450 ml of absolute methylenechloride was mixed dropwise over a period of 30 minutes with a solution of 119.4 gm (1.1 mols) of ethyl chloroformate in 600 ml of absolute methylene chloride. The temperature rose to 40° C. The mixture was then stirred for 4 hours at room temperature. The resulting suspension was vigorously shaken, once with 500 ml of water accompanied by the addition of some ice, twice with 500 ml each of dilute hydrochloric acid, and then twice with 500 ml each of water. After drying with magnesium sulfate, the organic phase was suction-filtered, and the brown filtrate was filtered through 50 gm of silicagel. Concentration by evaporation was then effected in a rotary evaporator at 40° C. This gives 178.5 gm of a colorless oily substance in a yield of 90.5%, which is immediately further reacted.

(c)
8-Benzyl-3-(4-trifluoromethyl-phenyl)-3-nortropanol methane sulfonate

A solution of 38.3 gm of p-bromo-benzotrifluoride (0.17 mol) in 100 ml of ether was added dropwise over a period of 10 minutes to 100 ml of a 1.6 N butyl lithium solution in hexane (0.16 mol), in an atmosphere of nitrogen at −35° C. in 200 ml of ether. After 5 minutes, 25.8 gm (0.12 mol) of 8-benzyl-nortropinone in 150 ml of ether were added very rapidly at −40° C. The reaction mixture was allowed to stand for one hour at −40° to −10° C. and was then carefully added to 200 ml of water containing 10 gm of ammonium chloride. The ether phase was separated, washed once with 100 ml of 1 N ammonium chloride and twice with 100 ml each of water. After drying over magnesium sulfate, the solution was suction-filtered, filtered through 200 gm of silicagel and concentrated by evaporation. The residue was dissolved in 25 ml of ethanol, mixed with a molar quantity of alcoholic methanesulfonic acid and a little ether. After some time the methanesulfonate crystallized out, which was filtered off and thoroughly washed with alcohol/ether. 37.3 gm of methanesulfonate were obtained with a yield of 68% of theory and a melting point of 250° C.

| $C_{21}H_{22}F_3NO \times CH_3SO_3H$ (mol. wt.: 457.44). | | | |
|---|---|---|---|
| C | H | F | N |
| Calc.: 57.76%; | 5.73%; | 12.46%; | 3.06% |
| Found: 57.63%; | 5.51%; | 12.50%; | 2.86%. |

The following compounds were prepared in analogous manner:

| | M.P. °C. |
|---|---|
| 8-benzyl-3-phenyl-3-nortropanol methanesulfonate | 220 |
| 8-benzyl-3-(4-fluoro-phenyl)-3-nortropanol methanesulfonate | 221 |
| 8-benzyl-3-(4-methyl-phenyl)-3-nortropanol hydrochloride | 237 |
| 8-benzyl-3-(4-methoxy-phenyl)-3-nortropanol hydrochloride | 196 |
| 8-benzyl-3-(3-trifluoromethyl-phenyl)-3-nortropanol methanesulfonate | 229–230 |

(d)
8-Ethoxycarbonyl-3-(4-chlorophenyl)-3-nortropanol 100 ml of a 1.6 M solution of butyl lithium in hexane were introduced into 200 ml of absolute ether. 32.5 gm (0.17 mol) of p-chloro-bromobenzene in 100 ml of ether were added dropwise at −35° C. in an atmosphere of nitrogen over a period of 10 minutes. After stirring for 5 minutes, 23.7 gm (0.12 mol) of freshly prepared 8-ethoxycarbonyl-nortropinone in 150 ml of ether were very rapidly added thereto. The temperature rose to −15° C. The resulting suspension was again cooled to −35° C. and then within 1½ hours heated to +10° C. The solution was carefully decomposed with 200 ml of water, while buffering with 10 gm of ammonium chloride. The ether phase was washed three times with 100 ml each of water. The organic phase was then dried with magnesium sulfate, suction-filtered and concentrated by evaporation in a rotary evaporator at 40° C. The residue was dissolved in 250 ml of methylene chloride/methanol (98:2), and the solution was filtered through 500 gm of silicagel and concentrated by evaporation. The residue was crystallized from ether/petroleum ether (40:60) and yielded 13.6 gm of white crystals, corresponding to a yield of 36.6%, with a melting point of 115° C.

| $C_{16}H_{20}ClNO_3$ (mol. wt.: 309.79) | | | |
|---|---|---|---|
| C | H | Cl | N |
| Calc.: 62.03%; | 6.51%; | 11.45%; | 4.52% |
| Found: 62.32%, | 6.65%; | 11.40%; | 4.47%. |

The following compounds were prepared in analogous manner:

| | M.P. °C. |
|---|---|
| 8-ethoxy-carbonyl-3-(4-chloro-3-trifluoromethyl-phenyl)-3-nortropanol | 167 |
| 8-ethoxycarbonyl-3-phenyl-3-nortropanol | 104 |

(e) 3-(Trifluoromethyl-phenyl)-3-nortropanol methanesulfonate 14 gm (0.031 mol) of 8-benzyl-3-(4-trifluoromethyl-phenyl)-3-nortropanol methanesulfonate were dissolved in 140 ml of methanol, the solution was mixed with 1.4 gm of 5% palladium-on-charcoal, and the mixture was hydrogenated at 5 bar at 50° C. After 2 hours, the hydrogen uptake was complete. The warm solution was suction-filtered and concentrated by evaporation in a rotary evaporator at 50° C. The residue was crystallized from isopropanol. 9.6 gm of white crystals were obtained, corresponding to a yield of 85.4%, with a melting point of 273° C.

| $C_{14}H_{16}F_3NO \times CH_3SO_3H$ (mol. wt.: 367.38) | | | |
|---|---|---|---|
| C | H | F | N |
| Calc.: 49.04%; | 5.49%; | 15.52%; | 3.81% |
| Found: 48.85%; | 5.22%; | 15.76%; | 3.61. |

The following compounds were obtained in analogous manner:

| | M.P. °C. |
|---|---|
| 3-phenyl-3-nortropanol methanesulfonate | 216–217 |
| 3-(4-fluoro-phenyl)-3-nortropanol methanesulfonate | 229 |
| 3-(4-methyl-phenyl)-3-nortropanol hydrochloride | 252 |
| 3-(4-methoxy-phenyl)-3-nortropanol hydrochloride | 216 |
| 3-(3-trifluoro-phenyl)-3-nortropanol methanesulfonate | 207 |

(f) 3-(4-Chloro-phenyl)-3-nortropanol hydrochloride 18.6 gm (0.06 mol) of 8-ethoxycarbonyl-3-(4-chlorophenyl)-3-nortropanol were stirred, accompanied by refluxing, for 70 hours together with 19.4 gm (0.35 mol) of potassium hydroxide in a mixture of 190 ml of isopropanol and 12.5 ml of water. 200 ml of water were then added, followed by neutralization with glacial acetic acid. After stirring for half an hour, the mixture was concentrated by evaporation in vacuo in a rotary evaporator. The residue was dissolved in 150 ml of 10% methanesulfonic acid, and the solution was shaken twice with 100 ml each of ether. 9 gm of the starting compound were recovered from this ether phase.

After making the acid aqueous phase alkaline with concentrated potassium hydroxide and extracting it three times with 150 ml each of methylene chloride containing 5% butanol, evaporation of the acid aqueous phase yielded a residue which was dissolved in ethanol and mixed with a molar quantity of ethanolic hydrochloric acid. After adding a little ether, 6.3 gm of the hydrochloride crystallized out with a yield of 38.3% and a melting point of 271° C.

| $C_{13}H_{16}ClNO \times HCl$ (mol. wt.: 274.19) | | | |
|---|---|---|---|
| C | H | Cl | N |
| Calc.: 56.94%; | 6.25%; | 25.86%; | 5.11% |
| Found: 57.10%; | 6.29%; | 25.87%; | 5.12%. |

The following compounds were prepared in analogous manner:

| | M.P. °C. |
|---|---|
| 3-phenyl-3-nortropanol hydrochloride | 216–217 |
| 3-(4-chloro-3-trifluoromethylphenyl)-3-nortropanol methanesulfonate | 195 |

(g) N-(4,4-Bis-4'-fluorophenylbutyl)-nortropinone hydrochloride 16.1 gm (0.1 mol) of nortropinone hydrochloride were heated for 4 hours to 100° C., accompanied by stirring, with 30.9 gm (0.11 mol) of 4,4-bis-4'-fluorophenylbutyl chloride, 25.4 gm (0.3 mol) of sodium bicarbonate and 5 gm of potassium iodide in 250 ml of dimethyl formamide. The solvent was then removed in a rotary evaporator at 70° C. The residue was taken up in 200 ml of ethyl acetate and washed twice with 100 ml each of water. The organic phase was dried over sodium sulfate and filtered through 10 gm of silicagel. The filtrate was evaporated in a rotary evaporator. The residue was dissolved in ethanol, and the solution was mixed with a slight excess of 0.1 m ethanolic hydrochloric acid. The hydrochloride crystallized out and was recrystallized from ethanol. 18.6 gm of the title compound were obtained with a yield of 45.7% and a melting point of 210° C.

| $C_{23}H_{25}F_2NO \times HCl$ (mol. wt.: 405.90) | | | |
|---|---|---|---|
| C | H | Cl | N |
| Calc.: 68.05%; | 6.46%; | 8.74%; | 3.45% |
| Found: 68.02%; | 6.60%; | 8.84%; | 3.42%. |

(h) N-(4-Fluorophenyl-4-hydroxy-butyl)-nortropinone hydrochloride 16.2 gm (0.1 mol) of nortropinone hydrochloride were heated at 100° C. for 3 hours, accompanied by stirring, with 26.9 gm (0.11 mol) of the ethylene ketal of 4-chloro-4'-fluorophenyl-butyrophenone, 25.4 gm (0.3 mol) of sodium bicarbonate and 5 gm of potassium iodide in 250 ml of dimethylformamide. The solvent was then removed in a rotary evaporator at 70° C. The residue was taken up in 200 ml of ethyl acetate, and the solution was washed twice with 100 ml each of water, dried and concentrated by evaporation. The residue was dissolved in 500 ml of 2 N hydrochloric acid, accompanied by the addition of 500 ml of ethanol, and the mixture was heated for 1 hour at 50° C. while stirring. The solution was then concentrated by evaporation at 50° C. in a rotary evaporator.

The residue was made alkaline with 50 ml of concentrated ammonia, while cooling with ice, and then extracted three times with 100 ml each of methylene chloride. The organic phase was dried over sodium sulfate and filtered through 10 gm of silicagel. The filtrate was evaporated in a rotary evaporator. The residue was dissolved in ethanol, mixed with a slight excess of 0.1 M ethanolic hydrochloric acid, and the hydrochloride crystallized out. The mixture was suction-filtered, and the filter cake was recrystallized from ethanol. 17.5 gm of the title compound were obtained with a yield of 53.8% and a melting point of 173° C.

| $C_{17}H_{20}FNO_2 \times HCl$ (mol. wt.: 325.81). | | | |
|---|---|---|---|
| C | H | F | N |
| Calc.: 62.67%; | 6.50%; | 5.83%; | 4.30% |
| Found: 62.46%; | 6.47%; | 5.82%; | 4.23%. |

PREPARATION OF END PRODUCTS OF THE FORMULA I

EXAMPLE 1

8-(4-p-Fluorophenyl-4-oxo-butyl)-3-(4-chloro-phenyl)-3-nortropanol hydrochloride by methods A and D 27.4 gm (0.1 mol) of 3-(4-chloro-phenyl)-3-nortropanol hydrochloride were heated for 5 hours at 100° C., accompanied by stirring, with 26.9 gm (0.1 mol) of the ethylene ketal of 4-chloro-4'-fluorophenyl-butyrophenone, 25.4 gm (0.3 mol) of sodium bicarbonate and 5 gm of potassium iodide in 250 ml of dimethylformamide. The solvent was then removed at 70° C. in a rotary evaporator. The residue was taken up in 200 ml of ethyl acetate, and the solution was washed twice with 100 ml each of water and concentrated by evaporation. The residue was dissolved in a mixture of 500 ml of 2 N hydrochloric acid and 500 ml of ethanol. The resulting solution was heated for 30 minutes at 50° C. After cooling, the solution was evaporated, and the residue was made alkaline with 50 ml of concentrated ammonia, while cooling with ice, and the mixture was extracted three times with 100 ml each of methylene chloride. The organic phase was dried over sodium sulfate and filtered through 10 gm of silica gel. The filtrate was evaporated in a rotary evaporator. The residue was dissolved in 50 ml of ethanol, the solution was mixed with 0.1 mol of ethanolic hydrochloric acid and then with ether, until turbidity just disappeared again. 24.5 gm of the title compound were obtained with a 56% yield and a melting point of 244° C.

| $C_{23}H_{25}ClFNO_2 \times HCl$ (mol. wt.: 438.36) | | | | |
|---|---|---|---|---|
| C | H | Cl | F | N |
| Calc.: 63.01%; | 5.98%; | 16.18%; | 4.33%; | 3.20% |

| -continued |
|---|
| $C_{23}H_{25}ClFNO_2 \times HCl$ (mol. wt.: 438.36) |

| | C | H | Cl | F | N |
|---|---|---|---|---|---|
| Found: | 62.88%; | 5.64%; | 15.76%; | 4.28%; | 2.91%. |

The compounds of the formula

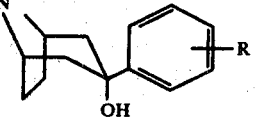

shown in the following table were prepared in analogous manner:

TABLE I

| Example | Ar | X | R | M.P. °C. | Salt |
|---|---|---|---|---|---|
| 2 | phenyl | >CO | H | 228 | HCl |
| 3 | 4-F-phenyl | >CO | H | 229 | HCl |
| 4 | 4-CH$_3$-phenyl | >CO | H | 217 | HCl |
| 5 | 4-CH$_3$O-phenyl | >CO | H | 211–212 | HCl |
| 6 | 2-furyl | >CO | H | 268 | HCl |
| 7 | 2-thienyl | >CO | H | 249 | HCl |
| 8 | pyridyl | >CO | H | 201–203 | 2 HCl |
| 9 | 4-F-phenyl | >CH—(4-F-phenyl) | H | 237 | HCl |
| 10 | 4-F-phenyl | >CH—C≡N | H | 199–200 | HCl |
| 11 | 4-F-phenyl | —O— | H | 143 | HCl |
| 12 | 4-F-phenyl | —S— | H | 193–194 | HCl |

TABLE I-continued

| Example | Ar | X | R | M.P. °C. | Salt |
|---|---|---|---|---|---|
| 13 | 4-F-C6H4- | —NH— | H | 160 | 2 HCl |
| 14 | 4-F-C6H4- | \CH—OH | H | 146–148 | HCl |
| 15 | 4-F-C6H4- | \C(OH)(4-F-C6H4) | H | 202 | HCl |
| 16 | 4-F-C6H4- | \C(CN)(4-F-C6H4) | H | 265–266 | HCl |
| 17 | 4-F-C6H4- | \CO | 4-CF3 | 210 | CH3SO3H |
| 18 | 4-F-C6H4- | \CH—C≡N | 4-CF3 | 144 | CH3SO3H |
| 19 | 4-F-C6H4- | \CH(4-F-C6H4) | 4-CF3 | 252 | CH3SO3H |
| 20 | 4-F-C6H4- | \CH—OH | 4-CF3 | 232 | HCl |
| 21 | 4-F-C6H4- | \C(OH)(4-F-C6H4) | 4-CF3 | 262 | HCl |
| 22 | 4-F-C6H4- | \C(CN)(4-F-C6H4) | 4-CF3 | 280 | HCl |
| 23 | 4-F-C6H4- | \CO | 4-F | 226 | CH3SO3H |
| 24 | 4-F-C6H4- | \CH—CN | 4-F | 199 | CH3SO3H |
| 25 | 4-F-C6H4- | \CH(4-F-C6H4) | 4-F | 225 | CH3SO3H |

TABLE I-continued

| Example | Ar | X | R | M.P. °C. | Salt |
|---|---|---|---|---|---|
| 26 | 4-F-C6H4- | >CH-OH | 4-F | 227 | HCl |
| 27 | 4-F-C6H4- | >C(OH)(4-F-C6H4) | 4-F | 215 | HCl |
| 28 | 4-F-C6H4- | >C(CN)(4-F-C6H4) | 4-F | 259 | HCl |
| 29 | 4-F-C6H4- | >CH-CN | 4-Cl | 173 | CH3SO3H |
| 30 | 4-F-C6H4- | >CH(4-F-C6H4) | 4-Cl | 127 | Base |
| 31 | 4-F-C6H4- | —O— | 4-Cl | 238 | CH3SO3H |
| 32 | 4-F-C6H4- | —S— | 4-Cl | 204 | CH3SO3H |
| 33 | 4-F-C6H4- | —NH— | 4-Cl | 196 | 2 HCl |
| 34 | 2-thienyl | >CO | 4-Cl | 197 | CH3SO3H |
| 35 | C6H5- | >CO | 4-Cl | 228–229 | HCl |
| 36 | 4-Cl-C6H4- | >CO | 4-Cl | 273 | HCl |
| 37 | 4-Br-C6H4- | >CO | 4-Cl | 220 | CH3SO3H |
| 38 | 4-CH3-C6H4- | >CO | 4-Cl | 227 | CH3SO3H |

TABLE I-continued

| Example | Ar | X | R | M.P. °C. | Salt |
|---|---|---|---|---|---|
| 39 | 4-CH₃O-C₆H₄- | >CO | 4-Cl | 205 | CH₃SO₃H |
| 40 | 4-F-C₆H₄- | >CH—OH | 4-Cl | 219 | HCl |
| 41 | 4-F-C₆H₄- | >C(OH)(4-F-C₆H₄) | 4-Cl | 227 | HCl |
| 42 | 4-F-C₆H₄- | >C(CN)(4-F-C₆H₄) | 4-Cl | 258 | HCl |
| 43 | 4-F-C₆H₄- | >CO | 4-Cl + 3-CF₃ | 183 | CH₃SO₃H |
| 44 | C₆H₅- | >CO | 4-Cl + 3-CF₃ | 202 | CH₃SO₃H |
| 45 | 2-thienyl | >CO | 4-Cl + 3-CF₃ | 240 | HCl |
| 46 | 4-F-C₆H₄- | >CH(4-F-C₆H₄) | 4-Cl + 3-CF₃ | 117 | Base |
| 47 | 4-F-C₆H₄- | —O— | 4-Cl + 3-CF₃ | 189 | CH₃SO₃H |
| 48 | 4-F-C₆H₄- | —S— | 4-Cl + 3-CF₃ | 170 | CH₃SO₃H |
| 49 | 4-F-C₆H₄- | —NH— | 4-Cl + 3-CF₃ | 184–185 | 2 HCl |
| 50 | 4-F-C₆H₄- | >CH—C≡N | 4-Cl + 3-CF₃ | 120 | HCl |
| 51 | 4-F-C₆H₄- | >CH—OH | 4-Cl + 3-CF₃ | 238 | HCl |

TABLE I-continued

| Example | Ar | X | R | M.P. °C | Salt |
|---|---|---|---|---|---|
| 52 | 4-F-C₆H₄- | -C(OH)(CH₃)-C₆H₄-4-F | 4-Cl + 3-CF₃ | 145–147 | HCl |
| 53 | 4-F-C₆H₄- | -C(CN)(CH₃)-C₆H₄-4-F | 4-Cl + 3-CF₃ | 300 | HCl |
| 54 | 4-F-C₆H₄- | >CH-CO- | 3-CF₃ | 219 | CH₃SO₃H |
| 55 | C₆H₅- | >CH-CO- | 3-CF₃ | 247–248 | HCl |
| 56 | 4-F-C₆H₄- | >CH-CH(C₆H₄-4-F)- | 3-CH₃ | 123–125 | Base |
| 57 | 4-F-C₆H₄- | -O- | 3-CF₃ | 194 | CH₃SO₃H |
| 58 | 4-F-C₆H₄- | -S- | 3-CF₃ | 192 | CH₃SO₃H |
| 59 | 4-F-C₆H₄- | -NH- | 3-CF₃ | 202–203 | 2 HCl |
| 60 | 2-thienyl | >CH-CO- | 3-CF₃ | 176 | CH₃SO₃H |
| 61 | 4-F-C₆H₄- | >CH-C≡N | 3-CF₃ | 172–173 | CH₃SO₃H |
| 62 | 4-F-C₆H₄- | >CH-OH | 3-CF₃ | 231 | HCl |
| 63 | 4-F-C₆H₄- | -C(OH)(-)-C₆H₄-4-F | 3-CF₃ | 207 | HCl |
| 64 | 4-F-C₆H₄- | -C(CN)(-)-C₆H₄-4-F | 3-CF₃ | 285 | HCl |

TABLE I-continued
| Example | Ar | X | R | M.P. °C. | Salt |
|---|---|---|---|---|---|
| 65 | 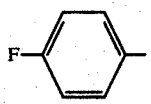 | CO | 4-CH₃ | 203 | CH₃SO₃H |
| 66 | 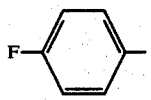 | CH—C≡N | 4-CH₃ | 194 | CH₃SO₃H |
| 67 | 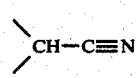 | 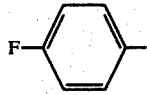CH—⟨C₆H₄⟩—F | 4-CH₃ | 227 | CH₃SO₃H |
| 68 | 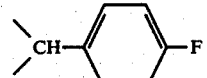 | —O— | 4-CH₃ | 215 | CH₃SO₃H |
| 69 | 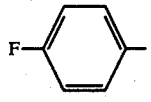 | —S— | 4-CH₃ | 181 | CH₃SO₃H |
| 70 | 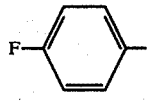 | —NH— | 4-CH₃ | 212 | 2 HCl |
| 71 | 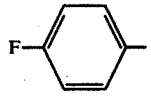 | 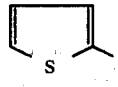CO | 4-CH₃ | 205 | CH₃SO₃H |
| 72 |  | 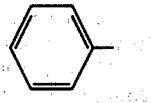CO | 4-CH₃ | 180 | CH₃SO₃H |
| 73 |  | 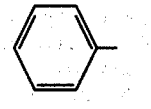CO | 4-OCH₃ | 143 | CH₃SO₃H |
| 74 |  | 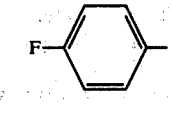CO | 4-OCH₃ | 166 | CH₃SO₃H |
| 75 |  | 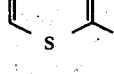CO | 4-OCH₃ | 184 | CH₃SO₃H |
| 76 |  | 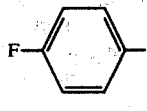CH—C≡N | 4-OCH₃ | 152 | CH₃SO₃H |
| 77 | 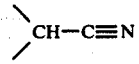 | 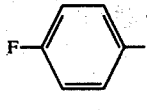CH—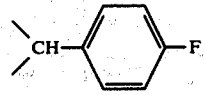—F | 4-OCH₃ | 195 | CH₃SO₃H |

TABLE I-continued

| Example | Ar | X | R | M.P. °C. | Salt |
|---|---|---|---|---|---|
| 78 | F-◯- | —O— | 4-OCH₃ | 177 | CH₃SO₃H |
| 79 | F-◯- | —S— | 4-OCH₃ | 172 | CH₃SO₃H |
| 80 | F-◯- | —NH— | 4-OCH₃ | 191 | 2 HCl |
| 81 | F-◯- | >CH—OH | 4-OCH₃ | 130 | HCl |
| 82 | F-◯- | >C(OH)-◯-F | 4-OCH₃ | 207 | HCl |
| 83 | F-◯- | >C(C≡N)-◯-F | 4-OCH₃ | 219 | HCl |

EXAMPLE 84

N-(4,4-Bis-p-fluorophenyl-butyl)-3-(4-fluoro-phenyl)-3-nortropanol methanesulfonate by method B In an atmosphere of nitrogen, 50 ml of 0.16 M solution of butyl lithium in hexane were introduced into 100 ml of ether, and the solution was mixed over a period of 10 minutes at −35° C. with a solution of 14.9 gm (0.085 mol) of p-fluoro-bromobenzene in 50 ml of ether. After vigorous stirring for 5 minutes at −35° C., a solution of 14.8 gm (0.04 mol) of N-(4,4-bis-4'-fluorophenyl-butyl)-nortropinone in 70 ml of ether was rapidly added, and the mixture was allowed to react for one hour at this temperature. The solution was then added to 100 ml of water, accompanied by the addition of 50 gm of ammonium chloride. The ether phase was washed three times with 50 ml each of water, dried over magnesium sulfate and evaporated. The residue was suspended in 200 ml of petroleum ether, and the solution was decanted. The residue was dissolved in ethanol. The addition of a molar quantity of methane-sulfonic acid in ethanol caused the methanesulfonate title compound to crystallize out, which was recrystallized from a little ethanol. 12.4 gm of the product were obtained with a yield of 55.1% and a melting point of 226° C. (identical with Example 25).

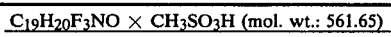

| | C | H | F | N |
|---|---|---|---|---|
| Calc.: | 64.15%; | 6.10%; | 10.15%; | 2.49% |
| Found: | 64.37%; | 6.12%; | 9.84%; | 2.36%. |

EXAMPLE 85

N-(4,4-Bis-4'-fluorophenyl-4-hydroxy-butyl)-3-(4-fluorophenyl)-3-nortropanol hydrochloride by method C In an atmosphere of nitrogen, 50 ml (0.08 mol) of a solution of n-butyl lithium in hexane were introduced into 100 ml of absolute ether. At −35° C., a solution of 14.9 gm (0.085 mol) of p-fluoro-bromobenzene in 50 ml of ether was added dropwise thereto over a period of 10 minutes. After another 5 minutes, a solution of 7.2 gm (0.025 mol) of N-(4-fluorophenyl-4-oxo-butyl)-nortropinone base in 30 ml of ether was rapidly added dropwise over a period of 5 minutes. At −40° to −25° C., the mixture was allowed to react for one hour. The resulting suspension was poured into 100 ml of water containing 40 gm of ammonium chloride. The ether phase was separated, washed three times with 50 ml each of water, dried and evaporated. The residue was mixed by stirring with 200 ml of petroleum ether (b.p. 40° to 60° C.), and the liquid was decanted. The residue was dissolved in ethanol, the solution was mixed with ethanolic hydrochloric acid, and the reaction product was caused to crystallize by adding ether. The product was recrystallized several times from alcohol/ether. 1.4 gm of the hydrochloride title compound was obtained with a yield of 10.8% and a melting point of 215° C. The compound was identical with that of Example 27.

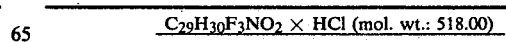

| | C | H | F | N |
|---|---|---|---|---|
| Calc.: | 67.24%; | 6.03%; | 11.00%; | 2.70% |

-continued

| $C_{29}H_{30}F_3NO_2 \times HCl$ (mol. wt.: 518.00) | | | |
|---|---|---|---|
| C | H | F | N |
| Found: 67.26%; | 6.13%; | 10.95%; | 2.54%. |

The compounds of the present invention, that is, those embraced by formula I and their non-toxic, pharmacologically acceptable acid addition salts, have useful pharmacodynamic properties. More particularly, they exhibit the typical activity spectrum of neuroleptics (major tranquilizers) in warm-blooded animals such as rats, and are therefore useful as CNS-depressants, sedatives and tranquilizers for the treatment of psychoses. In comparison to the known, structurally related neuroleptic compound haloperidol [1-(3-p-fluorobenzoyl-propyl)-4-chlorophenyl-4-hydroxy-piperidine], the compounds of the instant invention exhibit a more favorable activity profile.

The properties of the compounds were investigated, using the apomorphine climbing test on mice in accordance with B. Costall et al., Europ. J. Pharmacol. 50, 39 ff. (1978). They have powerful apomorphine-antagonizing actions, which many times exceed the action of haloperidol. According to the state of the art, these properties lead to the expectation of neuroleptic effects in humans. Information on the side-effects, such as sedation or coordination disturbances, were obtained by means of the following test arrangements: The motility test on mice according to T. H. Svensson and G. Thieme, Psychopharmacol. (Berlin), 14, 157 ff. (1969) which gives information on sedation; and the ataxia test on the rotating rod (Rotarod) on mice according to N. W. Dunham and T. S. Miya, J. Amer. Pharm. Assoc. Sci. Ed., 46, 208 ff. (1957) which gives details on disturbances of the motor coordination. With regard to side-effects, the compound according to the invention have a more favorable behavior than the comparison substance haloperidol.

Binding studies on rats were used for the biochemical characterization of the compounds according to the invention. Thus, the substances were investigated in the $^3$H-spiroperidol binding test (binding test with tritium-labeled 8-[3-(p-fluorobenzoyl)-propyl]-1-phenyl-1,3,8-triazaspiro[4,5]decan-4-one) on synaptosome preparations from rat brain (striatum) according to J. Creese, D. R. Burt and S. H. Snyder, Science 188, 1217 (1975). They have a much better binding behavior than haloperidol and also have a powerful neuroleptic action. In addition, tests were carried out in connection with the α-adrenergic and α-adrenolytic properties, using tritium-labeled 2-[2-(2',6'-dimethoxy-phenone)-ethylamino-methyl]-benzodioxane hydrochloride, which is an α-adrenergic antagonist. In this binding test, the compounds according to the invention have characteristics which are greatly superior to those of haloperidol [D. C. U'Prichard, D. A. Greenberg and S. A. Snyder, Mol. Pharmacol. 13, 454 ff. (1977)]. Tests for muscarinic anticholinergic binding properties were carried out in binding tests, using tritium-labeled 3-quinuclidinylbenzilate according to Yamamura and S. H. Snyder, Proceed. Nat. Acad. Sci. USA, 71, 1725–1729 (1974). Some of the compounds according to the invention exhibit more powerful anticholinergic binding properties than haloperidol.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.007 to 0.143 mgm/kg body weight, preferably 0.014 to 0.071 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 86

Coated tablets

The tablet core is compounded from the following ingredients:

| | |
|---|---|
| 8-(4-p-Fluorophenyl-4-hydroxy-butyl)-3-(4-chloro-phenyl)-3-nortropanol hydrochloride | 2.0 parts |
| Lactose | 28.5 parts |
| Corn starch | 17.0 parts |
| Gelatin | 2.0 parts |
| Magnesium stearate | 0.5 parts |
| Total | 50.0 parts |

Preparation:

The active ingredient, the lactose and the corn starch are intimately admixed with each other, the mixture is moistened with an aqueous 10% solution of the gelatin, and the moist mass is granulated by passing it through a 1 mm-mesh screen. The granulate is dried at 40° C., again passed through the screen, and admixed with the magnesium stearate. The composition is compressed into 50 mgm-tablets which are subsequently coated with a thin shell consisting essentially of a mixture of sugar, titanium dioxide, talcum and gum arabic. The coated tablets are finally polished with beeswax. Each coated tablets is an oral dosage unit composition containing 50 mgm of the active ingredient.

EXAMPLE 87

Tablets

The tablet composition is compounded from the following ingredients:

| | |
|---|---|
| 8-(4-p-Fluorophenyl-4-hydroxy-butyl)-3-(4-chloro-phenyl)-3-nortropanol hydrochloride | 2.0 parts |
| Lactose | 55.0 parts |
| Corn starch | 38.0 parts |
| Soluble starch | 4.0 parts |
| Magnesium stearate | 1.0 parts |
| Total | 100.0 parts |

Preparation:

A mixture of the active ingredient and the magnesium stearate is moistened with an aqueous solution of the soluble starch, the moist mass is granulated by passing it through a screen, and the granulate is dried and then intimately admixed with the lactose and the corn starch. The composition is compressed into 100 mgm-tablets, each of which is an oral dosage unit composition containing 2 mgm of the active ingredient.

EXAMPLE 88

Suppositories

The suppository composition is compounded from the following ingredients:

| | | |
|---|---|---|
| 8-(4-p-Fluorophenyl-4-hydroxy-butyl)-3-(4-chloro-phenyl)-3-nortropanol hydrochloride | | 1.0 parts |
| Suppository base (e.g. cocoa butter | | 1699.0 parts |
| | Total | 1700.0 parts |

Preparation:

The finely powdered active ingredient is homogeneously blended with the aid of an immersion homogenizer into the suppository base which had been melted and cooled to 40° C. 1700 mgm-portions of the composition are filled into cooled suppository molds and allowed to harden therein. Each suppository is a rectal dosage unit composition containing 1 mgm of the active ingredient.

EXAMPLE 89

Hypodermic solution

The solution is compounded from the following ingredients:

| | | |
|---|---|---|
| 8-(4-p-Fluorophenyl-4-hydroxy-butyl)-3-(4-chloro-phenyl)-3-nortropanol hydrochloride | | 2.0 parts |
| Sodium chloride | | 18.0 parts |
| Distilled water | q.s. ad | 2000.0 parts by vol. |

Preparation:

The active ingredient and the sodium chloride are dissolved in the distilled water, the solution is filtered until free from suspended particles, and the filtrate is filled under aseptic conditions into 2 cc-ampules which are subsequently sterilized and sealed. The contents of each ampule are an injectable dosage unit composition containing 2 mgm of the active ingredient.

Any one of the other compounds embraced by formula I or a non-toxic, pharmacologically acceptable acid addition salt thereof may be substituted for the particular active ingredient in Examples 86 through 89. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

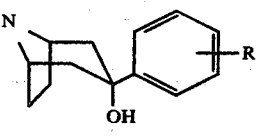

wherein
Ar is

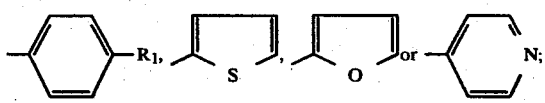

$R_1$ is hydrogen, fluorine, bromine, methyl or methoxy;
X is =CO, =CH—CN, =CH—OH, —O—, —S—, —NH—,

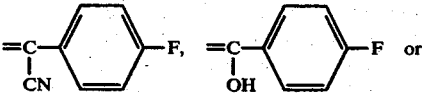

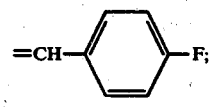

and
R is hydrogen, 4-fluoro, 4-chloro, 4-trifluoromethyl, 3-trifluoromethyl, 3-trifluoromethyl-4-chloro, 4-methyl or 4-methoxy;
or a non-toxic, pharmacologically acceptable acid addition salt thereof.

2. A compound of claim 1
wherein
Ar is 4-fluoro-phenyl;
X is =CO, =CH—CN, =CH—OH or

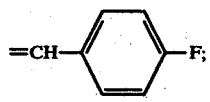

and
R is halogen;
or a non-toxic, pharmacologically acceptable acid addition salt thereof.

3. A compound of claim 1, wherein
A is 4-fluoro-phenyl;
X is =CO or =CH—CN; and
R is halogen;
or a non-toxic, pharmacologically acceptable acid addition salt thereof.

4. A compound of claim 1, which is 8-(4-p-fluorophenyl-4-oxo-butyl)-3-(4-chloro-phenyl)-3-nortropol or a non-toxic, pharmacologically acceptable acid addition salt thereof.

5. A neuroleptic pharmaceutical dosage unit composition consisting essentially of an inert pharmaceutical carrier and an effective neuroleptic amount of a compound of claim 1.

6. The method of depressing the central nervous system of a warm-blooded animal in need thereof, which comprises perorally, parenterally or rectally administering to said animal an effective neuroleptic amount of a compound of claim 1.

* * * * *